(12) United States Patent
Wilson

(10) Patent No.: US 8,530,830 B2
(45) Date of Patent: Sep. 10, 2013

(54) SENSING TECHNIQUES FOR ON-FARM ANALYSIS OF MILK COMPONENTS

(75) Inventor: Allan Walter Wilson, Hamilton (NZ)

(73) Assignee: Lely Patent N.V., Maassluis (NL)

( * ) Notice: Subject to any disclaimer, the term of this patent is extended or adjusted under 35 U.S.C. 154(b) by 0 days.

(21) Appl. No.: 13/271,267

(22) Filed: Oct. 12, 2011

(65) Prior Publication Data

US 2012/0138787 A1    Jun. 7, 2012

Related U.S. Application Data

(63) Continuation of application No. PCT/NZ2010/000065, filed on Apr. 12, 2010.

(30) Foreign Application Priority Data

Apr. 12, 2009   (NZ) .................................. 574228

(51) Int. Cl.
   *A01J 5/013*   (2006.01)
   *H01J 49/00*   (2006.01)

(52) U.S. Cl.
   CPC ........... *A01J 5/0131* (2013.01); *H01J 49/0027* (2013.01)
   USPC ......................... 250/282; 119/14.18; 250/287

(58) Field of Classification Search
   USPC ........................................................ 250/283
   See application file for complete search history.

(56) References Cited

U.S. PATENT DOCUMENTS

| | | | |
|---|---|---|---|
| 6,495,823 B1 * | 12/2002 | Miller et al. | 250/286 |
| 6,609,068 B2 * | 8/2003 | Cranley et al. | 702/24 |
| 6,806,463 B2 | 10/2004 | Miller et al. | |
| 7,030,372 B2 | 4/2006 | Miller et al. | |
| 7,091,481 B2 * | 8/2006 | Miller et al. | 250/288 |
| 7,162,971 B2 * | 1/2007 | Johannesson et al. | 119/14.18 |
| 2005/0233459 A1 | 10/2005 | Melker et al. | |

FOREIGN PATENT DOCUMENTS

| | | |
|---|---|---|
| NZ | 512435 A | 2/2003 |
| NZ | 531794 A | 2/2006 |

OTHER PUBLICATIONS

Hettinga, "Quality control of raw cows 'milk by headspace analysis—a new approach to mastitis diagnosis", chapter 7, pp. 92-105, PHD Thesis, 2009.*

Gursoy et al., "Preliminary study of ion mobility based electronic nose MGD-1 for discrimination of hard cheeses", Journal of Food Engineering, vol. 92, No. 2, pp. 202-207. Available online Nov. 12, 2008.*

Pan, L., M. Adams, and J. Pawliszyn. 1995. Determination of fattyacids using solid-phase microextraction. Analytical Chemistry 67:4396-4403.*

Elmore, J.S., M.A. Erbahadir, and D.S. Mottram. 1997. Comparison of dynamic headspace concentration on Tenax with solid phase microextraction for the analysis of aroma volatiles. Journal of Agricultural and Food Chemistry 45:2638-2641.*

(Continued)

*Primary Examiner* — Jack Berman
(74) *Attorney, Agent, or Firm* — Hoyng Monegier LLP; Coraline J. Haitjema; David P. Owen

(57) ABSTRACT

A method of analyzing milk components having the steps of collecting a milk sample, ionizing the milk sample, and using an ion mobility spectrometer to detect predetermined components within the ionized milk sample, wherein the ion mobility spectrometer is positioned within a milking system from which the milk sample is taken.

13 Claims, 7 Drawing Sheets

(56) References Cited

OTHER PUBLICATIONS

Grote, C. and J. Pawliszyn. 1997. Solid-phase microextraction for the analysis of human breath. Analytical Chemistry 69:587-596.*

Mariaca, R.G. and J.O. Bosset. 1997. Instrumental analysis of volatile (flavour) compounds in milk and dairy products. Lait 77:13-40.*

Marsili, R.T. 1999a. Comparison of solid-phase microextraction and dynamic headspace methods for the gas chromatographic-mass spectrometric analysis of light-induced lipid oxidation products in milk. Journal of Chromatographic Science 37:17-23.*

Marsili, R.T. 1999b. SPME-MS-MVA as an electronic nose for the study of off-flavors in milk. Journal of Agricultural and Food Chemistry 47:648-654.*

"Mass spectrometric ionization methods", Fraunhofer IVV. pp. 1-5. 2011.

Bathgate et al, "A novel electrospray-based ion mobility spectrometer", American J. of Physics, pp. 1111-1118, 2004.

Guevremont et al, "Atmospheric pressure ion focussing in a high-field asymmetric waveform ion mobility spectrometer", AIP review of Scientific Instruments, vol. 70, issue 2, 1999.

Hettinga, K, "Quality control of raw cows' milk by headspace analysis—a new approach to mastitis diagnosis", PHD Thesis, 2009.

Garrido-Delgado et al,"Use of ion mobility spectroscopy with an ultraviolet ionization source" Talanta v79 3 pp. 863-868, 2009.

Waine T, "Ch 3, Gas Sensing with MGD-1" non invasive soil property measurement for precision farming, Oct. 1999.

Waine T, "Ch 8, Conclusions and recommendations" non invasive soil property measurement for precision farming, Oct. 1999.

Guharay et al, Ion Mobility Spectrometry: Ion Source Development and Application in Physical and Biological Sciences, IEEE Transactions on Plasma Science, vol. 36, No. 4 Aug. 2008 p. 1458-1470.

International Search Report from PCT/NZ2010/000065 issued on Jul. 12, 2010.

* cited by examiner

SENSING TECHNIQUES FOR ON-FARM ANALYSIS OF MILK COMPONENTS

CROSS REFERENCE TO RELATED APPLICATIONS

This application is a continuation of PCT application number PCT/NZ2010/000065 filed on Apr. 12, 2010, which claims priority from New Zealand application number NZ 574228 filed on Apr. 12, 2009. Both applications are hereby incorporated by reference in their entireties.

BACKGROUND OF THE INVENTION

1. Field of the Invention

The invention relates generally to sensing techniques, and in particular, but not necessarily exclusively, the present invention relates to sensing techniques in relation to the dairy industry.

2. Description of the Related Art

Reference throughout the specification shall be made to the dairy industry, including all milking animals such as cows, sheep, horses, pigs, goats and camels. For ease of reference, the milking animal will be referred to as a cow.

The profitability of the dairy industry depends heavily upon the health of the milking animals and the composition of the milk itself. Consequently a number of sophisticated techniques have been developed to aid the dairy farmer in this area.

For example, it can be vitality important for a farmer to know whether a cow has mastitis which is an infection of the udder. This is generally detected on the farm using a variant of the Californian mastitis test (CMT). This involves taking a sample of the milk, introducing a reagent such as a surfactant, and then determining the resultant viscosity of the reagent/sample mix. In general, the greater the number of somatic cells within the milk sample, the greater resultant viscosity once the reagent is added. As can be appreciated, conducting such a test is labor intensive and not well suited to a milking shed environment.

An attempt to address these problems were made by the applicant in its New Zealand Patent Number 512435, which describes an automated means of conducting a similar test. However, this test only relates to one parameter of the milk. This means that additional sensors are required to measure other milk parameters, for example, fat, blood, and antibiotics.

Another problem is that an automated CMT still requires the use of a reagent. Dairy farmers in particular are adverse to the use of reagents because they:
  can lead to contamination of the equipment and/or the milk;
  need to be purchased in addition to the equipment; and
  add an extra step to the process, even if automated.

Optical sensors are known which do not require the addition of a reagent. Optical sensors can be useful in that they can detect more than one parameter of the milk, such as fat, protein and blood. Yet, there are limitations with optical sensors as they cannot be used to detect the presence of progesterone, antibiotics or bacterial cells indicating mastitis. Therefore, these sensors are still limited in their use.

Conductivity sensors have been used to determine the likelihood of mastitis. However, as with optical sensors these are not universal in their application.

It is possible to have a broad spectrum analyzer to determine a vast number of components in milk, such as a mass spectrometer or using NIR (near infra-red radiation). However, these devices are usually very expensive and are highly sensitive requiring laboratory equivalent conditions, certainly unlike the conditions found in a typical milking shed. In addition, NIR will not measure progesterone, antibiotics or bacterial metabolites.

Biosensor technologies can measure a wide range of analytes and chemicals. However, these devices use bioactive surfaces and compounds which are sensitive to temperature and external conditions and need to be regularly replaced. Such sensor technologies are also very expensive, require reagents which can be carcinogenic and need tight control of temperature and external conditions, which excludes them from practical use on a farm.

It should be appreciated that there is a need to be able to provide a sensing technique that:
  can characterize more than just a few milk components of interest;
  is relatively inexpensive;
  is reagent/consumable free; and
  is suited to a milking shed environment.

It is an object of the present invention to address the foregoing problems or at least to provide a useful choice.

BRIEF SUMMARY OF THE INVENTION

According to one aspect of the present invention there is provided a method of analyzing milk components having the steps of (a) collecting a milk sample, (b) ionizing the milk sample, and (c) using an ion mobility spectrometer to detect components of interest within the ionized milk sample. The method is characterized in that the ion mobility spectrometer is positioned within a milking system from which the milk sample was taken.

Accordingly to another aspect of the present invention there is provided an ion mobility spectrometer configured to operate within a milking system in accordance with the above method.

The milking system in the present device includes every aspect from the initial extraction of the milk from the animal up to and including the milk stored in the vat and associated derivatives thereof, including the vacuum line right up to the vacuum pump as it contains important analyzable substances.

Therefore the ion mobility spectrometer can be associated with any of the aspects and not necessarily be physically encased within a component of the milking system.

For example, components of interest can include any of the following components, namely blood, protein, fat, vitamins, progesterone, antibiotics, acetone, ketone bodies, bacterial volatiles, value-added proteins (lactoferrin), lactose, free-fatty acids, minerals, organic acids, free sugars not including lactose to name a few.

It is envisioned that the present invention could be used in relation to a number of milk components, preferably ones that give an indication of the health of the animal and/the composition of the milk. Alternatively the present invention could ascertain disease and metabolic states ie, mastitis, oestrus, ketogenesis, starvation, breeding value, weighted average productivity and performance.

The collection of the milk sample may be achieved by a number of ways.

In one embodiment of the present invention, the milk sample may be collected in gaseous form, for example in the head space of the milk line. Original analysis by other parties suggested that only a few volatiles are detectable with little significant differences found between them. This suggested that headspace sampling could be of limited use. However, recent work from the applicants showed unexpectedly good results when the head space was analyzed inline as opposed to offline as done previously.

Head space analysis allows the possibility of detecting a sub-set of compounds present within the milk matrix without needing to process the liquid components of milk. This greatly simplifies sampling and ionizing procedures as well as cleanliness requirements. On the other hand, liquid milk ionization allows a more complete profile of compounds found in the milk matrix to be determined. Therefore in preferred embodiments of the present invention it is envisioned that either a headspace sample will be extracted or liquid milk will be collected for ionization.

Suitable sampling methods include those discussed in the applicants NZ patent no. 512435 or NZ patent no. 531794 as well as ultrasonic fogging unit (self-sampling).

Farmers are most interested in data relating to individual animals. This can help determine:
  if diversion of milk is required (if a high level of mastitis or antibiotic);
  if diversion of the animal itself is required (for example if oestrus is indicated through progesterone levels);
  if special treatment to the animal is required (treatment of a disease); or
  the breeding value through the history of milk quality and volume from the animal.

Having regard to this, preferred embodiments of the present invention utilize milk samples which can be linked back to individual animals. Additionally it can be used to determine the current state of the whole herd and thus supply valuable herd management information.

In preferred embodiments, the milk sample collected is in liquid form and diverted from the main milk stream of individual animals through various means.

While it is envisioned that preferred embodiments of the present invention analyze milk samples on an individual animal basis, it is thought that some embodiments of the present invention may measure bulk samples such as the milk within a milk vat. For example, dairy companies pay out for, or decline milk on the quality of the bulk milk being collected. This may take into account antibiotic levels, somatic cell counts and fat/protein ratios. Therefore it would be useful if there could be provided a sensing technique that provides relevant data prior to milk collection by the milk tankers.

Depending on the milk components to be detected, care may need to be taken in the ionizing of the liquid milk sample. For example, milk has large fat molecules. It is highly possible that standard ionizing techniques would break apart these molecules leading to inaccurate readings of fat content. Therefore, one aspect of the present invention is the use of soft ionization techniques whereby charges are attached to the components, rather than removing electrons therefrom and possibly cleaving the molecules. Possible techniques include UV ionization, corona discharge, and atmospheric pressure ionization techniques described in http://www.ivv.fraunhofer.de/ms/ms-ionization.html.

A key aspect of the present invention is using an ion mobility spectrometer to detect the components of interest. This device has many advantages over the previous sensing techniques used. These advantages include:
  being reagent free;
  ability to detect various components;
  real time detection;
  mechanical simplicity;
  labour free.

Various types of ion mobility spectrometers can be used in relation to the present invention. These include variants of those discussed in Ben Bathgate, Eric C. S. Cheong, and Christopher J. Backhouse, "A Novel Electrospray-based Ion Mobility Spectrometer," Department of Electrical and Computer Engineering, University of Alberta, Edmonton, Alberta T6G 2V4, Canada; Roger Guevremont and Randy W. Purves, "Atmospheric Pressure Ion Focusing in a High-field Asymmetric Waveform Mobility Spectrometer," Institute for National Measurement Standards, National Research Council of Canada, Ottawa K1A 0R6, Canada; U.S. Pat. No. 7,030,372; U.S. Pat. No. 6,806,463; and U.S. Pat. No. 6,495,823.

In preferred embodiments, the IM spectrometer is based on the principles of time-of-flight or asymmetric fields. Preferred embodiments use a whole spectrum analysis conducted on the milk sample, rather than tuning the device to specific analytes as is done with the electronic noses such as the MGD-1 sensor described in T. Waine, "Non invasive soil property measurement for precision farming," Ch3 Gas Sensing with MGD-1 and Ch8 Conclusions, Cranfield University 1999.

There are a number of advantages to taking this approach. The first is that there is no second guessing as a consequence of the analysis being undertaken. The one set of data can be analyzed in many ways to obtain the required information. This is not possible with specifically tuned devices which could be tuned so to miss an important analyte.

By conducting a whole spectrum analysis, better indictors of disease can be provided as a combination of lower concentrations of particular analytes can be disease indicators. For example, there may be provided in some embodiments multi variant analyzes—possibly based on neural networks.

Devices that require specific tuning can be "fiddly" to implement. In the milking shed environment, the less precise calibration required the better.

A preferred gas sampling system samples every 200 µs. This enables sampling more often per unit of time than other techniques, and this obtains more information resulting in better resolution and discrimination. Preferred FAIMS (Field Asymmetric Ion Mobility Spectrometer) and TOF-IMS (Time of Flight Ion Mobility Spectrometer) devices are very sensitive so less sample is required to obtain the desired level of resolution.

BRIEF DESCRIPTION OF THE DRAWINGS

Further aspects of the present invention will become apparent from the following description which is given by way of example only and with reference to the accompanying drawings in which.

DESCRIPTION OF ILLUSTRATIVE EMBODIMENTS

The following is a description of certain embodiments of the invention, given by way of example only and with reference to the drawings.

Figure 1:
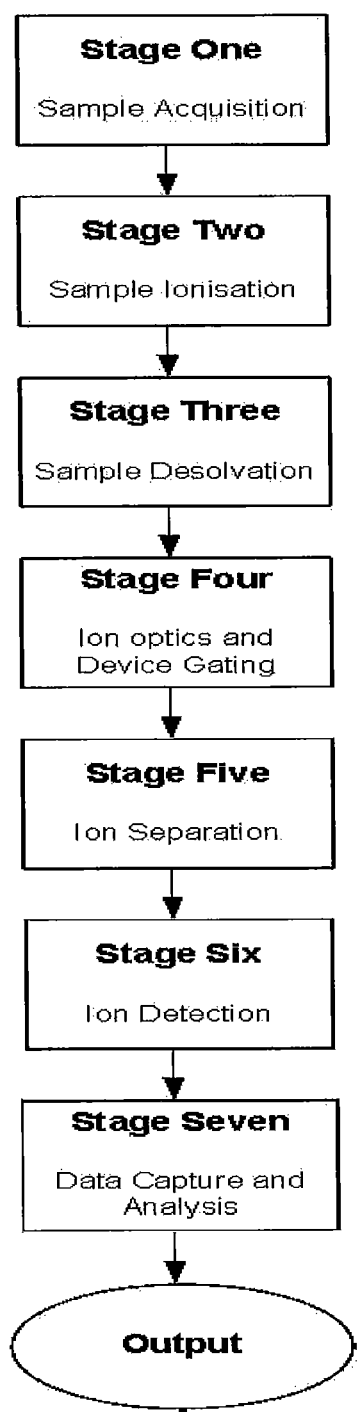
FIG. 1 is a flow chart illustrating various stages in the implementation of one embodiment of the present invention.

FIG. 1 illustrates a step by step process by which one embodiment of the present invention can be implemented. It is envisaged that the present invention will be implemented in a number of stages. Stage 1 is the acquisition of a suitable sample for ionization. In a preferred embodiment, ultrasonic frequencies are used to nebulise a small proportion of the milk. It is envisaged the nebulised milk will be particles in the order of 10 microns.

The nebulised milk components will then be passed through to an ionizer. In preferred embodiments, the ionization (Stage 2) will be in the form of a modified electrosprayer with the nebulised particles passing through a very fine High Voltage glass filter. The milk components will have electrons attached thereto or stripped therefrom in a form of soft ionization.

Stage 3 involves sample desolvation. This involves the extraction of the unimportant ions so that only ions of interest go through to Stage 4. For example, Stage 3 can include a dehumidification step with removal of water (solvent) therefrom.

Stage 4 relates to ion optics and device gating. It is at this stage that the filtering/focussing process relating to the ions is determined and what is introduced and when into the field of the ion mobility spectrometer. At this stage mathematical pseudorandom sequences can be introduced to convolve the gating and filtering sequences to aid in signal intensity and clarity at detection.

Stage 5 is a standard stage in the operation of an ion mobility spectrometer. This is the separation of the ions which occurs according to the operation of a particular spectrometer, whether a time of flight or FAIMS spectrometer is used.

Stage 6 involving ion detection may be performed in a number of ways. In some embodiments of the present invention, the ion detection may result from the use of specific sensors to capture known ions. However, as discussed above, in preferred embodiments a whole spectra is captured. The means by which the ion detection can occur can include the use of a Faraday cup/plate, micro channel plate, or a phosphor and CCD combination. Resolution may be either temporal, spatial or both.

Stage 7 is data capture and analysis. This may be achieved in many ways, for example through multivariate analysis, neural networks, whole spectra analysis or deconvolution.

Figure 2A:
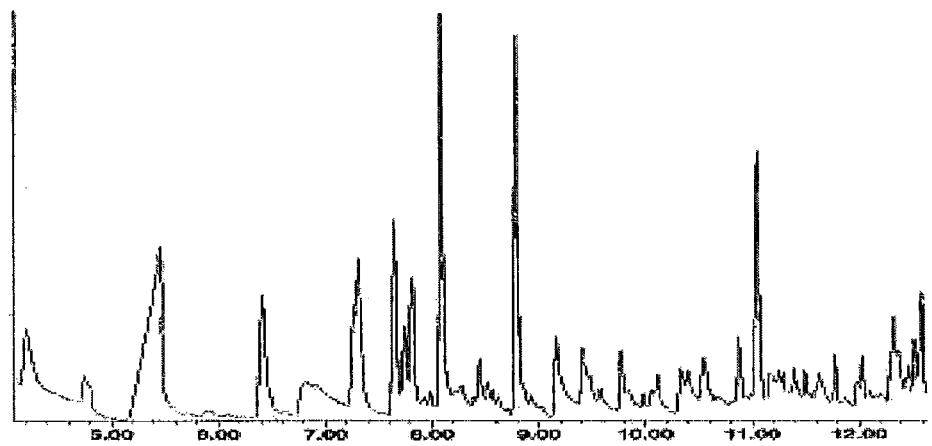
FIG. 2 illustrates the difference between inline and offline headspace captures.
Figure 2B:
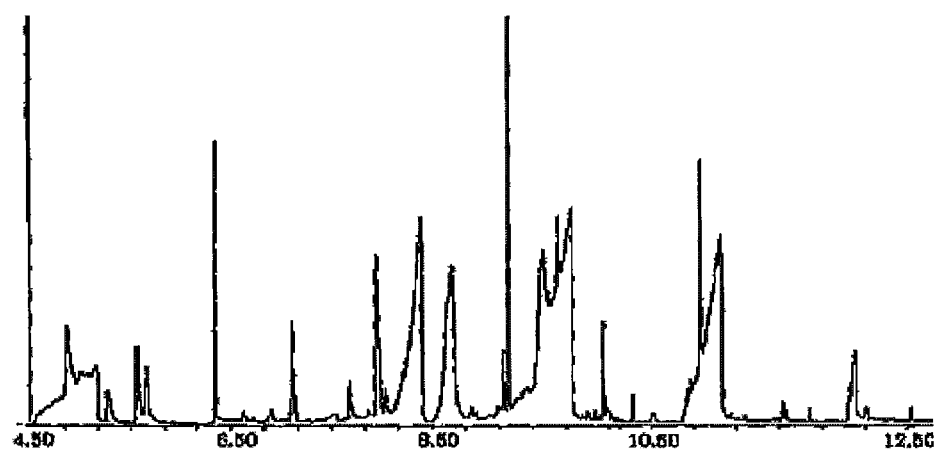

FIGS. 2A and 2B show the differences in volatiles captured using Inline headspace analysis (shown in FIG. 2A) versus Offline headspace analysis (shown in FIG. 2B). When the milk headspace is captured inline with the milking plant and analysed, an array of volatiles are detected, including extremely volatile compounds such as branched chain hydrocarbons (see T. Waine, "Non invasive soil property measurement for precision farming") not usually detected with offline procedures (K. Hettinga, "Quality control of raw cows' milk by headspace analysis—a new approach to mastitis diagnosis," Ch7 Discussion, Wageningen Universiteit 2009). Additionally some compounds that are usually non-volatile are detected above baseline, possibly due to the low-pressure environment of modern milking machinery.

Figure 3:
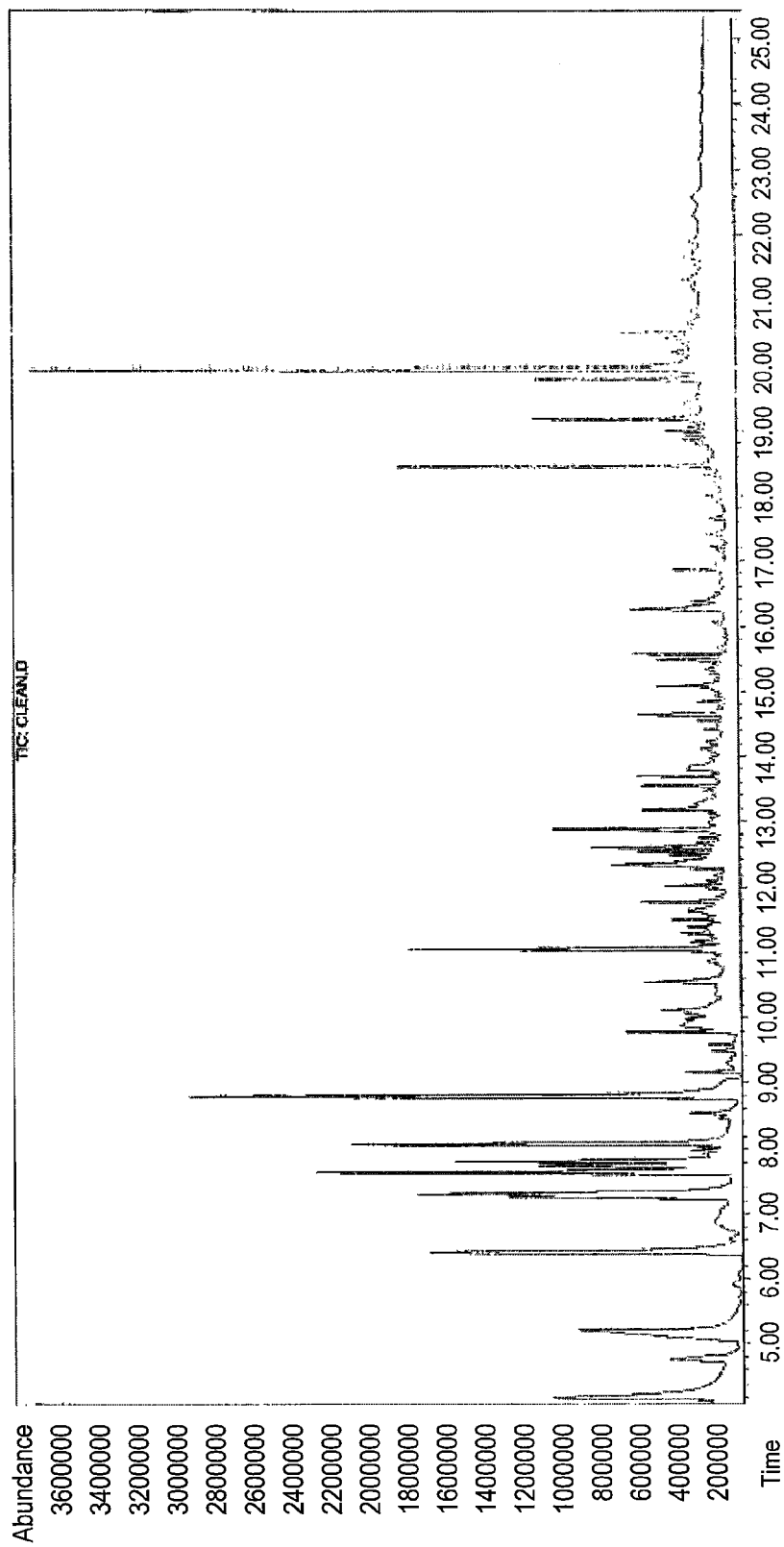
FIGS. 3 to 7 represent various spectra obtained from inline head space capture.

FIG. 3 is a spectrum collected from in-line sampling of a healthy cow.

Figure 4:
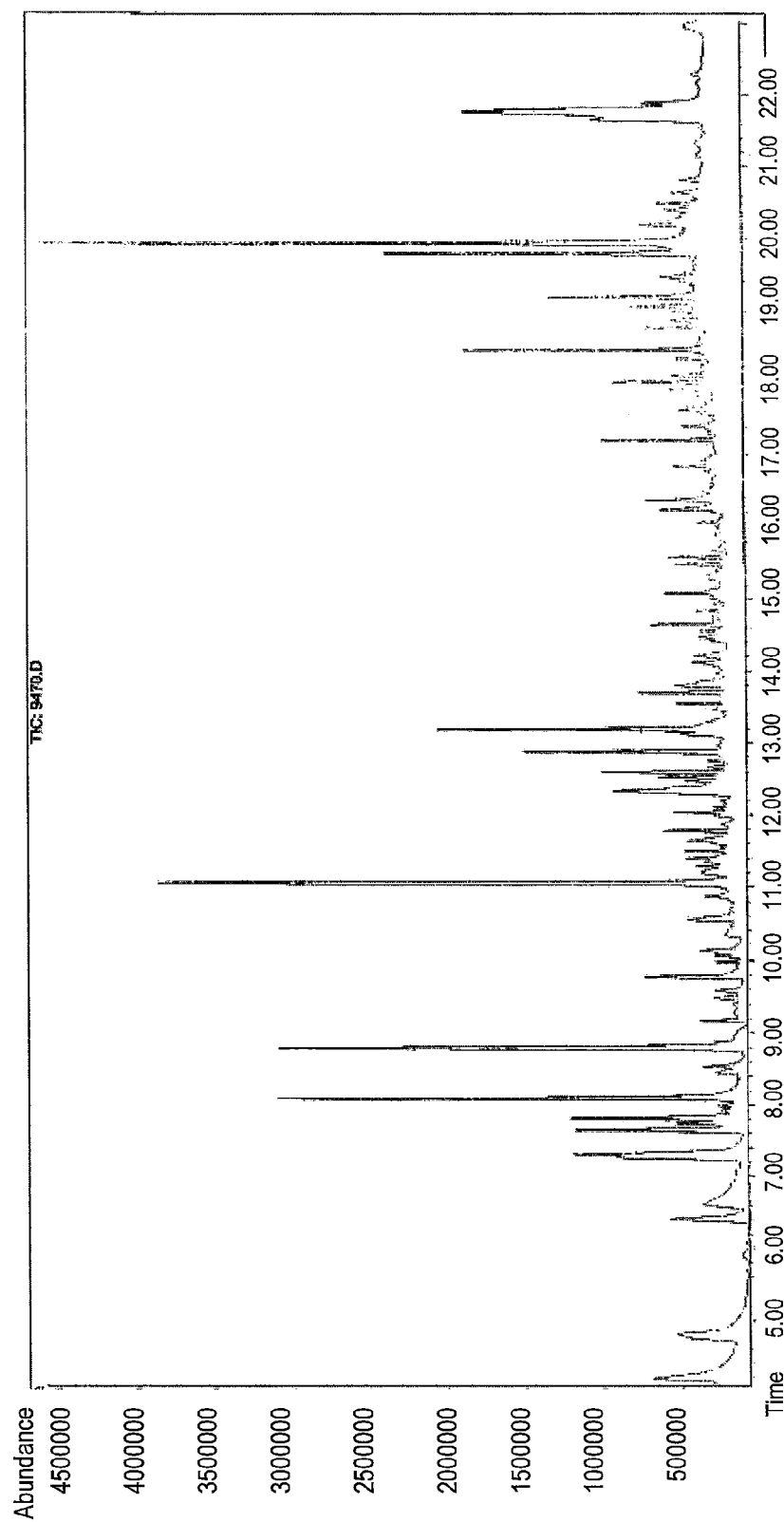
Figure 5:
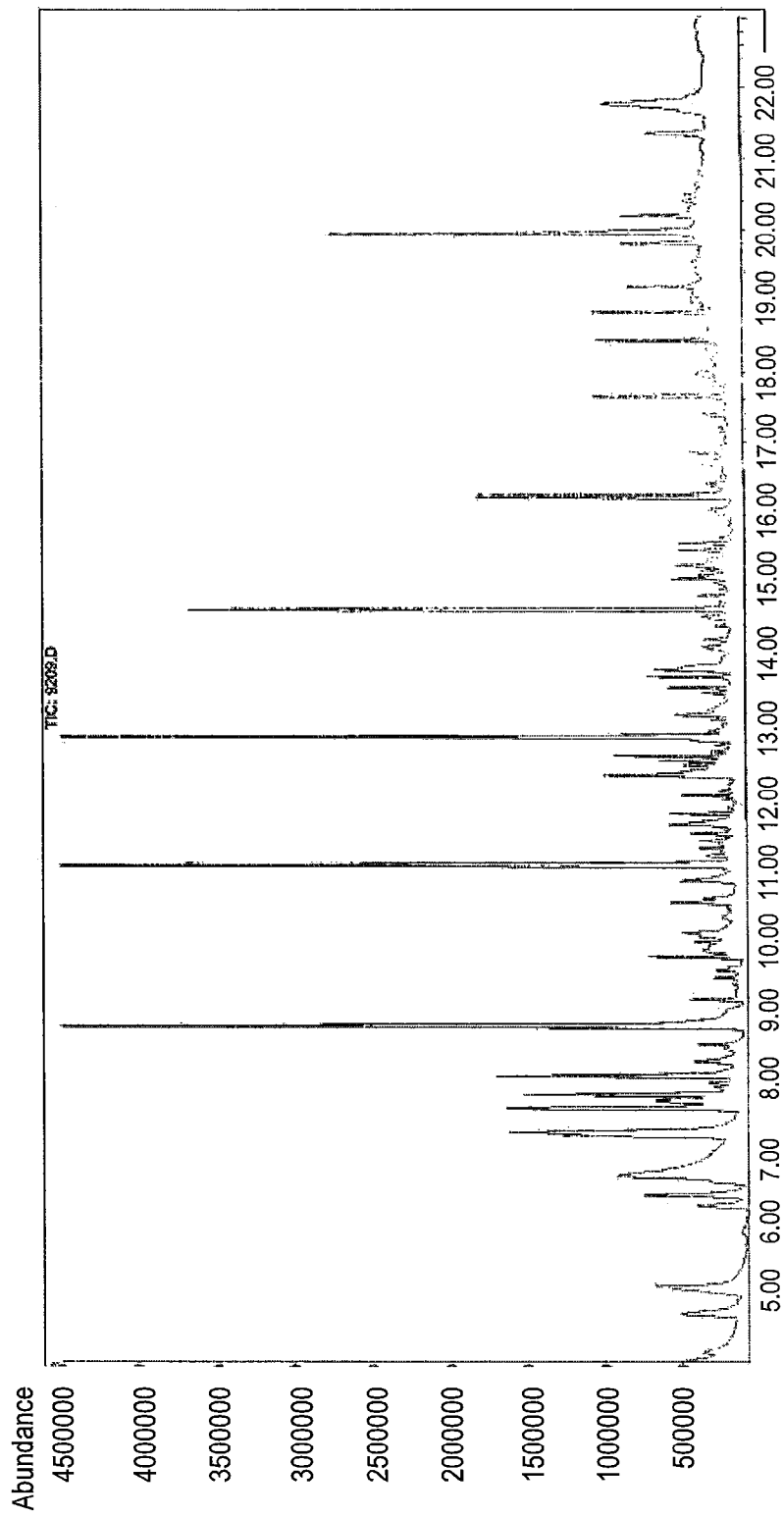

FIGS. 4 and 5 are spectra from cows recovering from mastitis and being treated with antibiotics.

Figure 6:
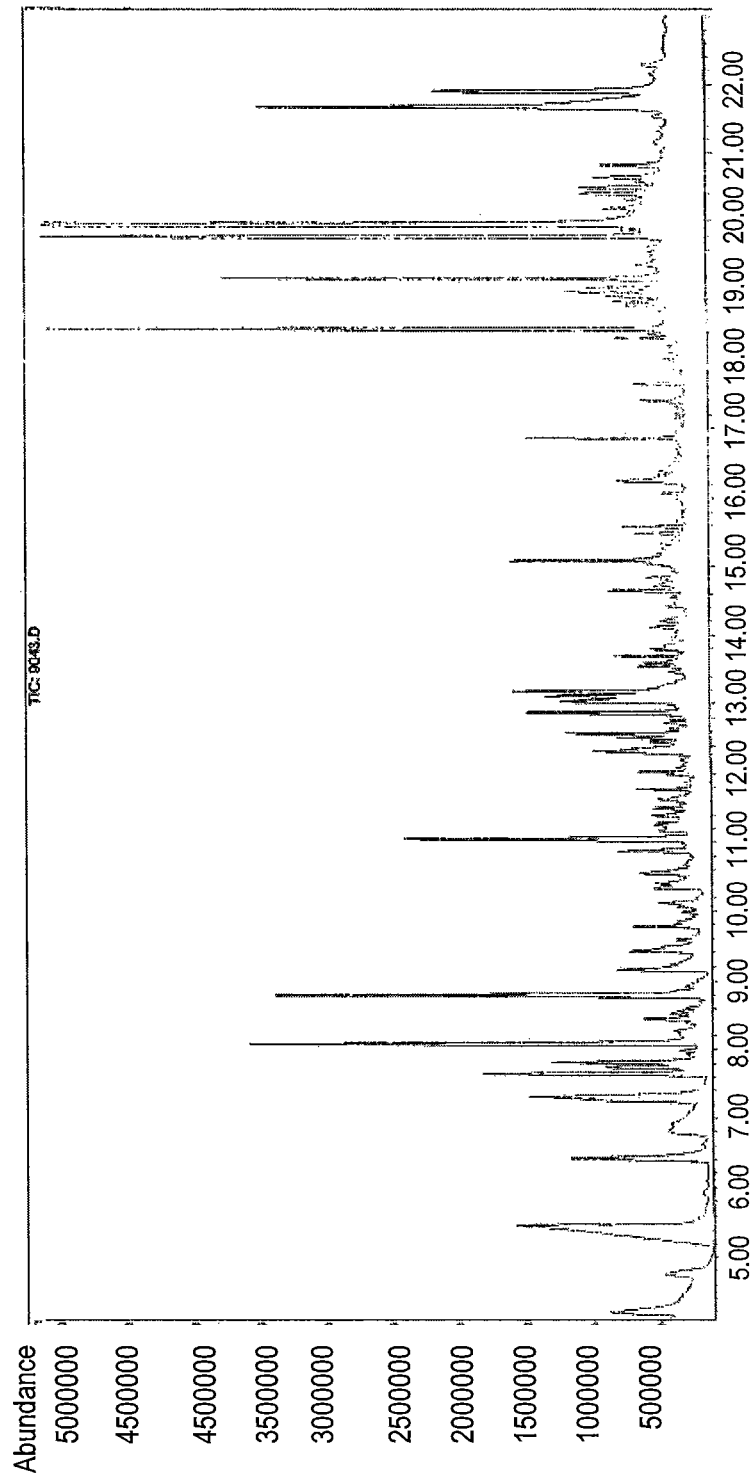
Figure 7:
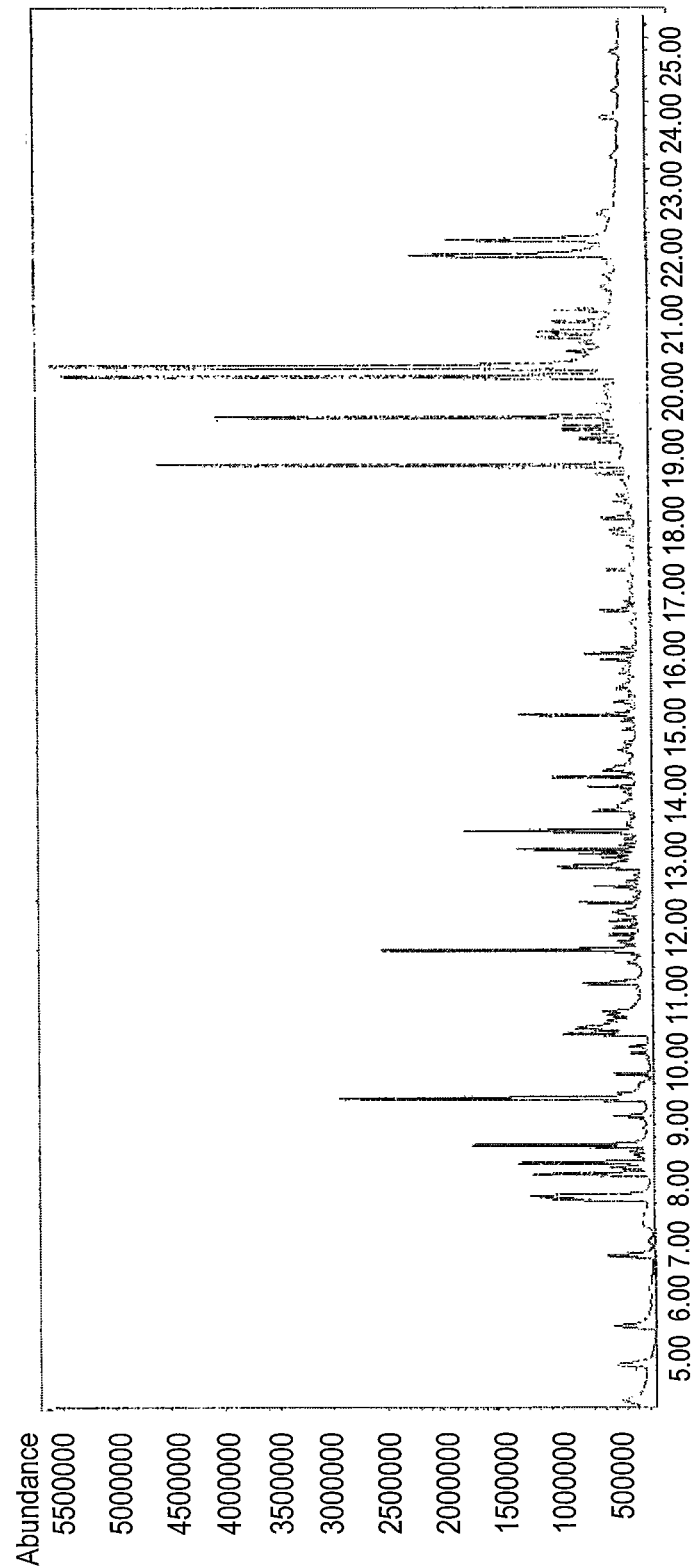

FIGS. 6 and 7 are spectra from untreated mastitis cows.

As can be seen, there are significant differences between the spectra as well as many different components detected, particularly as shown in FIG. 7.

All references, including any patents or patent applications cited in this specification are hereby incorporated by reference. No admission is made that any reference constitutes prior art. The discussion of the references states what their authors assert, and the applicants reserve the right to challenge the accuracy and pertinency of the cited documents. It will be clearly understood that, although a number of prior art publications are referred to herein, this reference does not constitute an admission that any of these documents form part of the common general knowledge in the art, in New Zealand or in any other country.

Throughout this specification, the word "comprise", or variations thereof such as "comprises" or "comprising", will be understood to imply the inclusion of a stated element, integer or step, or group of elements integers or steps, but not the exclusion of any other element, integer or step, or group of elements, integers or steps.

Aspects of the present invention have been described by way of example only and it should be appreciated that modifications and additions may be made thereto without departing from the scope thereof as defined in the appended claims.

What is claimed is:

1. A method of analysing milk components having the steps of:
    collecting a milk sample;
    ionizing the milk sample; and
    using an ion mobility spectrometer to detect predetermined components within the ionized milk sample;
    wherein the ion mobility spectrometer is positioned within a milking system from which the milk sample is taken.

2. A method as claimed in claim 1 wherein the milk components comprise one or more of blood, protein, fat, vitamins, progesterone, antibiotics, acetone, ketone bodies, bacterial volatiles, value added proteins, lactose, free-fatty acids, minerals, organic acids, and free sugars.

3. A method as claimed in claim 1, wherein the milk components indicate diseases and metabolic states comprising one or more of mastitis, estrus, ketogenesis, starvation, breeding value, weighted average productivity, and performance.

4. A method as claimed in claim 1, wherein the milk sample is collected in gaseous form.

5. A method as claimed in claim 4, wherein the milk sample is collected from the head space of the milk line.

6. A method as claimed in claim 1, wherein the milk sample is collected in liquid form.

7. A method as claimed in claim 1, wherein the milk sample is linked back to an individual animal.

8. A method as claimed in claim 1, wherein the milk sample is ionized using a soft ionization technique.

9. A method as claimed in claim 1, wherein the spectrometer operates on the principle of time of flight.

10. A method as claimed in claim 1, wherein the spectrometer operates on the principle of asymmetric fields.

11. A method as claimed in claim 1, wherein the step of using an ion mobility spectrometer to detect the predetermined components within the ionized milk sample is conducted using a whole spectrum analysis.

12. A method as claimed in claim 1, wherein the step of using an ion mobility spectrometer to detect the predetermined components within the ionized milk sample comprises a multivariate analysis.

13. An ion mobility spectrometer configured to operate within a milking system in accordance with the method as claimed in claim 1.

* * * * *